United States Patent [19]
Cubbage et al.

[11] Patent Number: 5,804,215
[45] Date of Patent: Sep. 8, 1998

[54] TRANSDERMAL PATCH DISPOSAL SYSTEM AND METHOD

[75] Inventors: Robert C. Cubbage, Kalamazoo; Robert B. Hamly, Kentwood; Todd C. Swartz, Wyoming, all of Mich.

[73] Assignee: L. Perrigo Company, Allegan, Mich.

[21] Appl. No.: 821,467

[22] Filed: Mar. 21, 1997

[51] Int. Cl.⁶ ............................... A61F 13/00; A61K 9/70
[52] U.S. Cl. ........................ 424/449; 424/443; 424/448; 424/445; 424/447
[58] Field of Search .................................. 424/449, 445, 424/446, 447, 448; 428/36.6

[56] References Cited

U.S. PATENT DOCUMENTS 5,470,529  11/1995  Wilfong et al. .................... 428/36.6

*Primary Examiner*—Thurman K. Page
*Assistant Examiner*—William E. Benston, Jr.
*Attorney, Agent, or Firm*—Price, Heneveld, Cooper, DeWitt & Litton

[57] ABSTRACT

A transdermal patch disposal member including a flexible, tear-resistant substrate having an area substantially larger than that of a transdermal patch for disposal. The substrate has one side at least partially coated with a self-sticking adhesive such that a transdermal patch can be placed on the substrate, which is folded upon itself to encapsulate the transdermal patch and prevent access to it. In a preferred embodiment of the invention, the disposal member is conveniently placed on a tear-away backing for storage until use. The method of disposing of a transdermal patch incorporating the present invention includes the placing of a transdermal patch on an adhesively coated substrate having a surface sufficiently large to provide a peripheral border around the transdermal patch and folding the disposing substrate upon itself for defining a pouch encapsulating the transdermal patch therein.

21 Claims, 3 Drawing Sheets

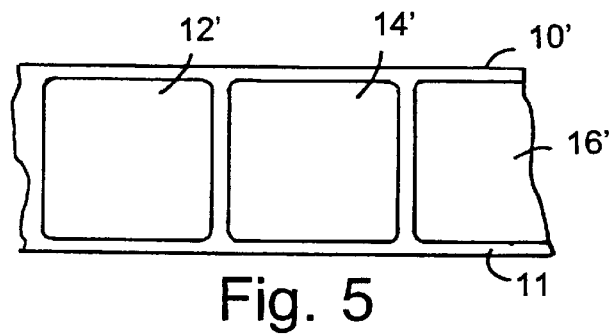
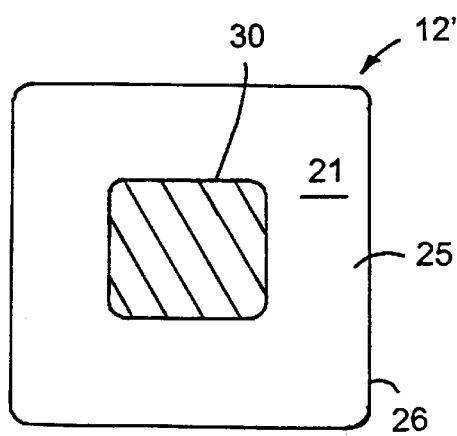
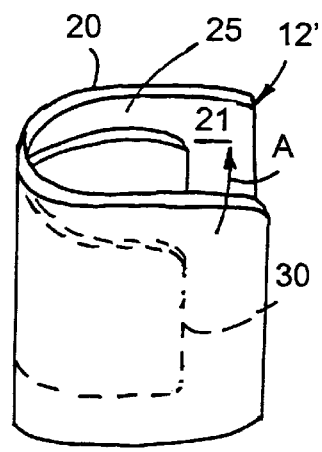
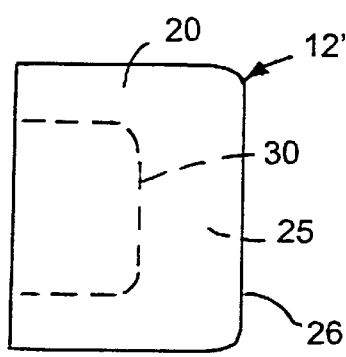
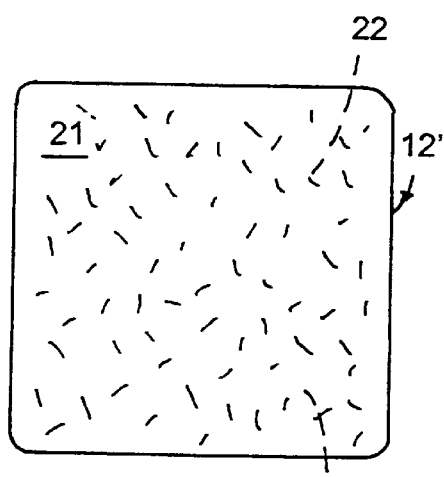

TRANSDERMAL PATCH DISPOSAL SYSTEM AND METHOD

BACKGROUND OF THE INVENTION

The present invention relates to a disposal structure for a used transdermal patch and the method of disposing of such a patch.

The utilization of transdermal patches for the controlled delivery of medication has become increasingly popular. Recently, transdermal patches have been commonly used for nicotine for those withdrawing from smoking. Although the patches have proven safe and effective in use for the delivery of a variety of medications, after their use, some residual medication remains and the safe disposal of such used transdermal patches can be a problem. If a used patch which still contains residual medication is simply placed in a wastebasket, small children or pets may gain access to such patches and chew on them or otherwise ingest the residual medication which can be harmful.

As a result, a variety of proposals have been suggested for the disposal of transdermal patches, most of which comprise the provision of disposal trays in which patches can be inserted but not easily removed. Although this disposal method may be appropriate for fixed locations, such as the home, when the users of such medications are traveling, particularly for brief periods of time carrying little luggage, use of bulky disposal trays is not practical. Accordingly, there exists a need for a system for safely disposing of used transdermal patches which have equal applicability in the home environment as well as for those traveling.

SUMMARY OF THE PRESENT INVENTION

The structure and method of the present invention solves the problem of safe disposal of transdermal patches by providing a disposal member made of a planar sheet of a flexible, tear-resistant material having an area substantially larger than that of a particular transdermal patch for disposal. The disposal member has one side at least partially coated with an aggressive self-sticking adhesive such that a transdermal patch can be placed on the disposal member, which is folded upon itself to encapsulate the transdermal patch preventing access to it. In a preferred embodiment of the invention, the disposal member is conveniently placed on a tear-away backing for storage until use.

Methods of disposing of a transdermal patch incorporating the present invention include the placing of a transdermal patch on an at least partially adhesively coated tear-resistant substrate having a surface sufficiently large to provide a peripheral border around the transdermal patch and folding the disposing substrate upon itself with the self-sticking adhesive defining a pouch enveloping the transdermal patch therein.

As can be appreciated, such a system and method allows an equal number of disposal members and patches to be provided in the same package for conveniently providing access to the user of both the transdermal patch and the disposal member. The disposal system of the present invention occupies little space and can be conveniently carried while traveling and yet provide a secure tamper-preventative encapsulation structure and method for disposal of transdermal patches at a relatively low cost.

These and other features, objects and advantages of the present invention will become apparent upon reading the following description thereof together with reference to the accompanying drawings.

BRIEF DESCRIPTION OF THE DRAWINGS

FIG. 5 is a plan view of an alternative embodiment of the invention in which a plurality of transdermal patch disposal members are removably positioned on a carrier web;

FIG. 6 is a plan view which illustrates the use of the alternative embodiment of the disposal member in connection with a used transdermal patch during a first step of the disposal process;

FIG. 7 is a perspective view which illustrates the further process of disposal of a transdermal patch utilizing the disposal member shown in FIG. 7;

FIG. 8 is a plan view of the disposal member showing its encapsulation of a transdermal patch therein ready for disposal;

FIG. 9 is a plan view of one side of a transdermal patch disposal member according to one embodiment of the invention;

DETAILED DESCRIPTION OF THE PREFERRED EMBODIMENT

Figure 1:
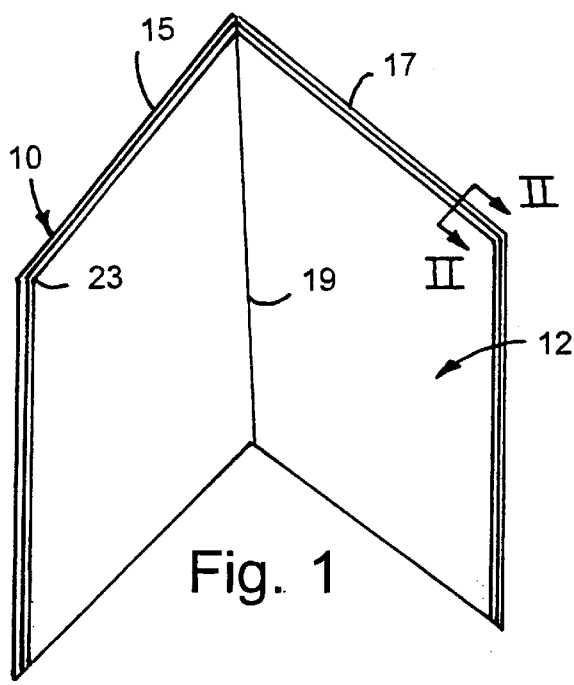
FIG. 1 is a plan view of a transdermal patch disposal member on a carrier.

Referring initially to FIG. 1, there is shown a backing member or carrier 10 to which an individual transdermal patch disposal member 12 is removably attached. The carrier 10 is preferably in the form of a planar, generally rectangular sheet with a left side 15 and a right side 17 divided by a fold line 19. Removably attached to the carrier 10 is the disposal member 12 which has a curved edge 23 to facilitate peeling the disposal member from the carrier. The combined rectangular carrier and disposal member is folded in half along fold line 19 to form a laminated card. The transdermal medication package contains an equal number of such cards and patches. The detail structure of the laminated carrier 10 and disposal member 12 is best seen in reference to FIG. 2 now described.

Figure 2:
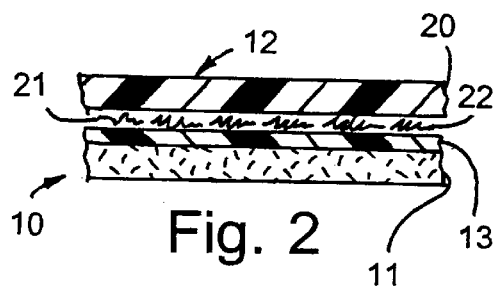
FIG. 2 is a greatly enlarged cross-sectional view of a section of the structure shown in FIG. 1 taken along section lines II—II of FIG. 1.

As seen in FIG. 2, each of the disposal members 12 comprises a substrate 20 which is an aggressive, tear-resistant film, such as a bi-axially oriented polypropylene, polyethylene laminated to paper, polyethylene terephthalate or Tyvek® made by DuPont. In one embodiment, the substrate 20 was bi-axially oriented polypropylene having a thickness of about from 2.8 to 4.2 mils±0.3 mils. Other thicknesses sufficient to prevent intrusion through the walls of the polymeric or composite substrate 20 can be employed. The inner surface 21 of the preferred substrate 20 is coated with an adhesive 22 which is aggressively self-sticking such that once the facing surface 21 of the disposal substrate 20 is pressed against itself, the disposal member can no longer be peeled apart. Generally, rubber-based adhesives have been found useful in this application and an adhesive such as I406 permanent rubber-based adhesive available from Fasson Avery Dennison Co. has been employed, although other adhesives with sufficient holding strength can be employed. Different substrates may also require different adhesives as is known to those skilled in the art. The adhesive 22 is applied to surface 21 in a conventional manner such as by spray coating, roll coating or the like.

Figure 3:
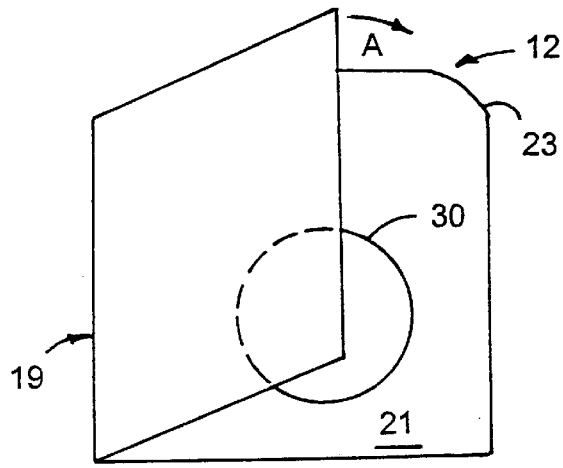
FIG. 3 is a perspective view illustrating the use of the disposal member and a used transdermal patch during the disposal process.
Figure 4:
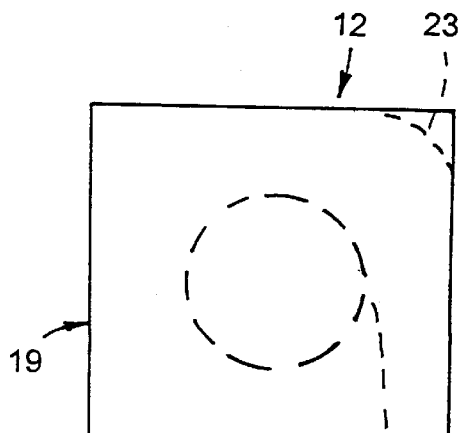
FIG. 4 is a plan view of the disposal member shown encapsulating a used transdermal patch.
Figure 10:
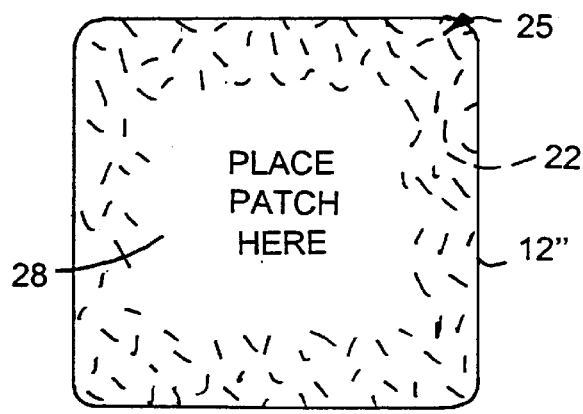
FIG. 10 is a plan view of one side of a transdermal patch disposal member according to another embodiment of the present invention.

The transdermal patch disposal members 12 thus formed are placed on the carrier 10 which can comprise a paper backing 11 with a non-sticky film 13 (FIG. 2) of a suitable release material such as silicone or be wax impregnated such that the transdermal patch disposal member 12 is held onto the carrier 10 but is relatively easily peeled off for use. In use, once a transdermal patch has expired, a card comprising carrier 10 and transdermal patch disposal member 12 thereon is removed from the package. Disposal member 12 is peeled away utilizing the cut-away corner 23 which exposes the carrier 10. A used transdermal patch 30 is placed on one of the facing sticky surfaces 21 of the disposal member 12, as seen in FIG. 3, and the left half of the disposal member 12 is closed onto itself along fold line 19 with the sticky facing surfaces 21 adhering to one another by pressing the outer peripheral edges of the disposal member 12 together encapsulating the transdermal patch 30, as shown in FIG. 4. In this embodiment, each half of the folded transdermal disposal member is substantially larger than the patch 30 for which it is employed so that the patch can be easily positioned on the disposal member without need for exact centering. Although the card-like structure shown in FIGS. 1–4 is preferred, other packaging systems can be utilized in the disposal system of the present invention as shown in the remaining drawing figures now described.

Referring to FIG. 5, there is shown a continuous web carrier 10' to which a plurality of individual transdermal patch disposal members 12', 14', 16' et seq. are removably attached. The carrier 10' may be in the form of a continuous web as shown or individual shapes somewhat larger than the transdermal disposal members 12', 14', 16' et seq. and stacked in a container along with the transdermal patches themselves or as a separate commodity. For a continuous web, the disposal members 12', 14', 16' et seq. can be formed in a convenient dispensing roll in a carton with a slot for withdrawing the web for access to a disposal member. As seen in FIG. 6, each of the identical members 12' are generally rectangular with a surface area significantly larger than that of a transdermal patch 30. Each of the disposal members comprises, as in the first embodiment, a substrate 20 made of a tear-resistant film, such as a bi-axially oriented polypropylene, having a thickness of from about 2–5 mils.

The inner surface 21 of the preferred substrate 20 is coated with an adhesive 22 which is aggressively self-sticking such that once the facing surface 21 of a disposal substrate 20 is pressed against itself, the disposal member can no longer be easily peeled apart. Generally, permanent rubber-based adhesives or their equivalent are employed. Different substrates may also require different adhesives as is known to those skilled in the art. The adhesive 22 is applied to surface 21 in a conventional manner such as by spray coating, roll coating or the like. The transdermal patch disposal members thus formed are placed on web carrier 10' which can comprise a paper backing 11 with anon-sticky film 13 as also seen in the first embodiment in FIG. 2. Film 13 is of a suitable release material such as silicone or paper 11 can be wax impregnated such that the transdermal patch disposal members 12', 14', 16' et seq. can be held onto the web but relatively easily peeled off for use. In the embodiment shown in FIGS. 5–10, the transdermal disposal members are shown in a generally square shape, although as can be appreciated, their particular shape is selected to dispose of a particular transdermal patch shape and can be rectangular, circular, triangular or any number of geometric shapes as long as their area is sufficiently larger than that of the transdermal patch as to allow encapsulation of the patch as now described in connection with FIGS. 6–8 and the method shown in FIG. 11.

In FIG. 6, a typical transdermal patch 30 is shown which has been used for the period of time provided for the dispensing of medication through the user's skin. Upon expiration of its use (typically one day), the patch is peeled off and must be safely disposed. In utilizing this invention, the patch 30 is placed generally in the center of the adhesive-coated side 21 of the disposal member 20 and is held there either by the adhesive 22 of the disposal member itself, if the entire surface 21 of the substrate 20 is so coated, or by the residual adhesive of the transdermal patch 30 itself or by a combination thereof. In any event, the used transdermal patch 30 is placed on the general center area of the disposal member 12' which is then folded, as illustrated in FIG. 7 by arrow A, upon itself until it forms a pouch sandwiching the transdermal patch therein, as seen in FIG. 8. In this position, the tear-resistant substrate 20 of the disposal member 12' is held upon itself around the peripheral border 25 between the edge of the transdermal patch 30 and the outer peripheral edge 26 of the substrate 20 thereby encapsulating the used transdermal patch 30 and preventing access, thereto.

In FIG. 9, one embodiment of the transdermal patch disposal member 12' is shown in which, the substrate surface 21 is entirely coated with an adhesive 22. In the FIG. 10 embodiment, only, the peripheral boundary 25 of a disposal member 12" is coated with adhesive 22. In this case, the residual adhesive of the transdermal patch 30 itself is employed for holding the patch in centered orientation on the disposal member until it is folded over as seen in FIG. 8. As can be appreciated, it is necessary for the encapsulation process only to have a sufficient area of adhesive adequate to prevent reopening of the disposal pouch so formed. The member 12" shown in FIG. 10 and the members 12 shown in FIGS. 1–4 and 12' in FIG. 9 each may include a centered indicia 28 instructing, the user on the placement of the transdermal patch such as the notation "Place Patch Here". Other indicia, such as an outline of the transdermal patch shape, can also be employed to indicate to the user that the patch is to placed in a center location on the disposal member.

Figure 11:
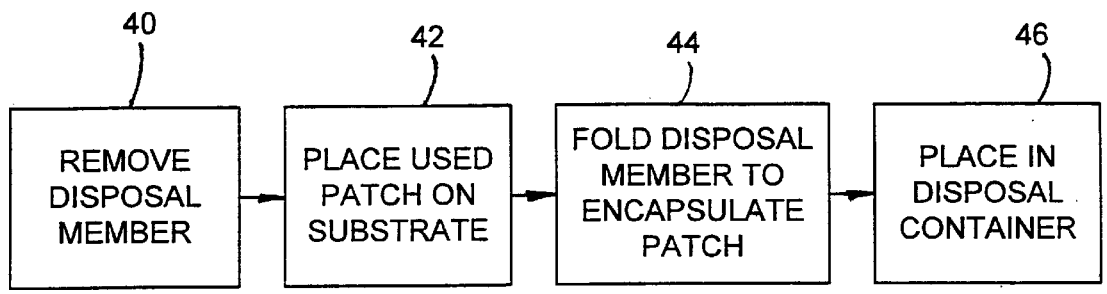
FIG. 11 is a flow diagram of the disposal of a transdermal patch according to the present invention.

The method of the use of the disposal system of the present invention is described in connection with FIG. 11 in which the disposal member is removed either from the card-like substrate of the first embodiment, the continuous web, or an individual backing member depending on the desired carrier shape employed for the disposal members as indicated by step 40 in FIG. 11. Next, the used transdermal patch 30 is placed on the disposal substrate, as indicated by block 42 and as shown in FIGS. 3 and 6 and held in position thereon by the adhesive of the transdermal patch itself or the adhesive 22 of the disposal substrate. The disposal member 12 is next folded, as illustrated in FIGS. 3 and 7, upon itself as indicated by step 44 with the adhesive surfaces 21 bonding together to encapsulate the patch as shown in FIGS. 4 and 8. Next, as indicated by step 46, the now-encapsulated patch can be disposed of in a conventional manner without fear of access by children or pets.

Figure 12:
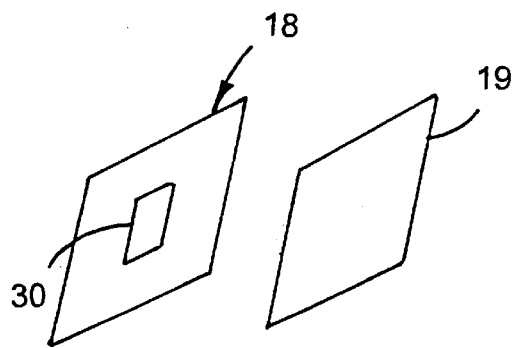
FIG. 12 is a perspective view of another embodiment of the invention.

Although the disposal members of the present invention are shown as receiving a patch in its planar condition, the disposal members can be made smaller if the transdermal patches are first folded upon themselves, thus reducing their size and reducing the size of the disposal members as well. As long as instructions are provided for the user which are sufficiently clear or graphically illustrated to provide safe use of such disposal members, smaller sized members can be employed. Also, in place of folding a disposal member upon itself, it is also possible to encapsulate a used patch utilizing a pair of facing disposal members 18 and 19, as shown in FIG. 12. In such case, instead of folding the member as shown in FIGS. 3 and 7, as discussed in step 42, two such members will be placed in overlying facing relationship to one another with the transdermal patch held between them. This structure also safely encapsulates a used transdermal patch for disposal.

It will become apparent to those skilled in the art that these and other modifications to the preferred embodiments of the invention as described herein can be made without departing from the spirit or scope of the invention as defined by the appended claims.

The embodiments owe invention in which an exclusive property or privilege is claimed are defined as follows:

1. A transdermal patch disposal member comprising:
    a generally planar sheet made of a tear-resistant flexible material; and
    an adhesive applied to at least an outer periphery of one surface of said sheet, wherein said sheet has a size sufficient to allow a transdermal patch to be placed upon said sheet such that when said sheet is folded said adhesive coated one surface bonds to itself for encapsulating the transdermal patch and preventing removal of the transdermal patch from said sheet of tear-resistant material.

2. The transdermal patch disposal member as defined in claim 1 wherein said adhesive surrounds a peripheral border of said substrate.

3. The transdermal patch disposal member as defined in claim 1 wherein a center area of said sheet includes indicia informing the user to place a transdermal patch in the center area of said substrate.

4. The transdermal patch disposal member as defined in claim 1 and further including a backing member for carrying said disposal member, said backing member allowing said disposal member to be peeled away for use.

5. The transdermal patch disposal member as defined in claim 4 wherein said backing member comprises a base and a non-stick film applied to said base and to which said disposal member is removably attached.

6. A method for disposing of used transdermal patches comprising the steps of:
    folding and placing a transdermal patch on a disposal member having an area greater than the area of the folded patch, said member including a tear-resistant film with at least a peripheral boundary coated with an adhesive;
    folding the disposal member upon itself; and
    pressing the edges of the folded member together such that the adhesive bonds to itself for encapsulating the patch for disposal.

7. The method as define in claim 6 and further including the steps of:
    releasably affixing the disposal member on a backing member prior to use; and
    peeling said disposal member from said backing member for use.

8. A transdermal patch disposal member comprising:
    a generally planar sheet made of tear-resistant material;
    an adhesive applied to at least a portion of one surface of said sheet; and
    indicia printed on said one surface of said sheet to allow a transdermal patch to be aligned with said indicia such that a patch can be placed upon said one surface which can subsequently be folded upon itself encapsulating the transdermal patch to prevent removal of the transdermal patch form said sheet of tear-resistant material.

9. The transdermal patch disposal member as defined in claim 8 wherein said adhesive surrounds a peripheral border of said one surface of said sheet.

10. The transdermal patch disposal member as defined in claim 9 wherein said indicia informs the user to place a transdermal patch in the area of said indicia.

11. The transdermal patch disposal member as defined in claim 10 and further including a backing member for carrying said substrate, said backing member allowing said substrate to be peeled away for use.

12. The transdermal patch disposal member as defined in claim 8 wherein said substrate is made of bi-axially oriented polypropylene.

13. The transdermal patch disposal member as defined in claim 12 wherein said adhesive is an rubber-based adhesive.

14. The transdermal patch disposal member as defined in claim 8 wherein said substrate is made of polyethylene terephthalate.

15. A transdermal patch disposal system comprising:
    a foldable sheet of material having one surface including a non-sticking film defining a backing member; and
    a sheet of tear-resistant material having an adhesive applied to at least a portion of one surface of said sheet, said sheet releasably positioned on said one surface of said backing member, wherein a transdermal patch can be placed upon said sheet of tear-resistant material when removed from said backing member and subsequently be folded upon itself for encapsulating a used transdermal patch.

16. The disposal system as defined in claim 15 wherein said non-sticking film comprises one of a silicone or wax material.

17. The disposal system as defined in claim 16 wherein a corner of said sheet of tear-resistant material is cut-away to facilitate removal of said sheet of said tear-resistant material from said backing member.

18. The disposal system as defined in claim 15 wherein sheet of tear-resistant material is made of bi-axially oriented polypropylene.

19. The disposal system as defined in claim 15 wherein said adhesive is a rubber-based adhesive.

20. The disposal system as defined in claim 15 wherein said sheet of tear-resistant material is made of polyethylene terephthalate.

21. The disposal system as defined in claim 15 wherein a center area of said sheet of tear-resistant material includes indicia informing the user to place a transdermal patch in the center area of said sheet of tear-resistant material.

\* \* \* \* \*

UNITED STATES PATENT AND TRADEMARK OFFICE
CERTIFICATE OF CORRECTION

PATENT NO. : 5,804,215
DATED : September 8, 1998
INVENTOR(S) : Robert C. Cubbage et al.

It is certified that error appears in the above-identified patent and that said Letters Patent is hereby corrected as shown below:

Column 3, line 63;
"anon-sticky" should be --a non-sticky--.

Column 3, lines 66 and 67;
After "paper 11" insert --and--.

Column 4, line 47;
"to placed" should be --to be placed--.

Column 6, claim 8, line 13;
"form" should be --from--.

Column 6, claim 13, line 28;
"is an" should be --is a--.

Column 6, claim 18, line 52;
After "wherein" insert --said--.

Signed and Sealed this

Eighteenth Day of May, 1999

Attest:

Q. TODD DICKINSON

*Attesting Officer*          *Acting Commissioner of Patents and Trademarks*